(12) United States Patent
Gray et al.

(10) Patent No.: US 6,362,322 B1
(45) Date of Patent: Mar. 26, 2002

(54) CONVERSION OF A WATSON-CRICK DNA TO A HOOGSTEEN-PAIRED DUPLEX

(75) Inventors: Donald M. Gray, Richardson; Gihan M. Hashem, Plano, both of TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/487,130

(22) Filed: Jan. 19, 2000

Related U.S. Application Data (63) Continuation-in-part of application No. 09/357,424, filed on Jul. 20, 1999.

(51) Int. Cl.[7] ............................ C07H 21/04; C12Q 1/68
(52) U.S. Cl. ........................................ 536/22.1; 435/6
(58) Field of Search ................................ 435/6, 5, 91.2, 435/91.1

(56) References Cited

U.S. PATENT DOCUMENTS 5,817,795 A * 10/1998 Gryaznov et al. ......... 536/24.3

* cited by examiner

*Primary Examiner*—Eggerton A. Campbell
(74) *Attorney, Agent, or Firm*—Locke Liddell & Sapp LLP; Robert E. Nail (57) ABSTRACT

A method is described for obtaining Hoogsteen-paired pyrimidine*purine duplexes, either by heating a triplex to dissociate a Watson-Crick paired pyrimidine strand or by linking two parallel strands at their 5' ends is disclosed. This duplex can be used as a new type of antisense molecule to pair with an RNA pyrimidine target sequence within an mRNA molecule. This duplex can also be used as a new type of antigene molecule to pair with a single-stranded DNA pyrimidine target sequence within the genome.

24 Claims, 3 Drawing Sheets

SEQUENCE LISTING

<160> NUMBER OF SEQ ID NOS: 17

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: synthetic
      nucleic acid

<400> SEQUENCE: 1
ctctctctct ctctctctct ctct                                              24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: synthetic
      nucleic acid

<400> SEQUENCE: 2
agagagagag agagagagag agag                                              24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: synthetic
      nucleic acid

<400> SEQUENCE: 3
ctctctctct ctctctctct ctct                                              24

<210> SEQ ID NO 4
<211> LENGTH: 24
<212> TYPE: RNA
<213> ORGANISM: Artificial Sequence
<220> FEATURE:
<223> OTHER INFORMATION: Description of Artificial Sequence: synthetic
      nucleic acid

<400> SEQUENCE: 4
cucucucucu cucucucucu cucu                                              24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: synthetic
      nucleic acid

<400> SEQUENCE: 5
agagagagag agagagagag agag                                              24

<210> SEQ ID NO 6
<211> LENGTH: 24
<212> TYPE: RNA
<213> ORGANISM: Artificial Sequence
<220> FEATURE:
<223> OTHER INFORMATION: Description of Artificial Sequence: synthetic
      nucleic acid

<400> SEQUENCE: 6

```
cucucucucu cucucucucu cucu                                        24
```

```
<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: synthetic
      nucleic acid
<223> OTHER INFORMATION: DNA and RNA strands can be linked at their
      5'-5' ends by normal chemical synthesis

<400> SEQUENCE: 7
ttttgaaggg agaaa                                                  15

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: synthetic
      nucleic acid
<223> OTHER INFORMATION: DNA and RNA strands can be linked at their
      5'-5' ends by normal chemical synthesis

<400> SEQUENCE: 8
ttttgaaggg agaaa                                                  15

<210> SEQ ID NO 9
<211> LENGTH: 11
<212> TYPE: RNA
<213> ORGANISM: Artificial Sequence
<220> FEATURE:
<223> OTHER INFORMATION: Description of Artificial Sequence: synthetic
      nucleic acid

<400> SEQUENCE: 9
uuucucccuu c                                                      11

<210> SEQ ID NO 10
<211> LENGTH: 15
<212> TYPE: DNA
<213> ORGANISM: Artificial Sequence
<220> FEATURE:
<223> OTHER INFORMATION: Description of Artificial Sequence: synthetic
      nucleic acid
<223> OTHER INFORMATION: DNA and RNA strands can be linked at their
      5'-5' ends by normal chemical synthesis

<400> SEQUENCE: 10
ttttgaaggg agaaa                                                  15

<210> SEQ ID NO 11
<211> LENGTH: 11
<212> TYPE: RNA
<213> ORGANISM: Artificial Sequence
<220> FEATURE:
<223> OTHER INFORMATION: Description of Artificial Sequence: synthetic
      nucleic acid

<400> SEQUENCE: 11
uuucucccuu c                                                      11

<210> SEQ ID NO 12
<211> LENGTH: 11
<212> TYPE: RNA
<213> ORGANISM: Artificial Sequence
```

<220> FEATURE:
<223> OTHER INFORMATION: Description of Artificial Sequence: synthetic
      nucleic acid
<223> OTHER INFORMATION: DNA and RNA strands can be linked at their
      5'-5' ends by normal chemical synthesis

<400> SEQUENCE: 12
cuucccucuu u                                                           11

<210> SEQ ID NO 13
<211> LENGTH: 11
<212> TYPE: DNA
<213> ORGANISM: Artificial Sequence
<220> FEATURE:
<223> OTHER INFORMATION: Description of Combined DNA/RNA Molecule:
      DNA/RNA Hoogsteen duplex
<223> OTHER INFORMATION: DNA and RNA strands can be linked at their
      5'-5' ends by normal chemical synthesis

<400> SEQUENCE: 13
cuucccucuu u                                                           11

<210> SEQ ID NO 14
<211> LENGTH: 11
<212> TYPE: DNA
<213> ORGANISM: Artificial Sequence
<220> FEATURE:
<223> OTHER INFORMATION: Description of Combined DNA/RNA Molecule:
      DNA/RNA Hoogsteen duplex as part of a triplex
<223> OTHER INFORMATION: DNA and RNA strands can be linked at their
      5'-5' ends by normal chemical synthesis

<400> SEQUENCE: 14
cuucccucuu u                                                           11

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: synthetic
      DNA triplex

<400> SEQUENCE: 15
ctctctctct ctagagagag agagctctct ctctct                                36

<210> SEQ ID NO 16
<211> LENGTH: 72
<212> TYPE: DNA
<213> ORGANISM: Artificial Sequence
<220> FEATURE:
<223> OTHER INFORMATION: Description of Artificial Sequence: synthetic
      DNA triplex

<400> SEQUENCE: 16
ctctctctct ctctctctct ctctagagag agagagagag agagagagct ctctctctct      60
ctctctctct ct                                                          72

```
<210> SEQ ID NO 17
<211> LENGTH: 72
<212> TYPE: DNA
<213> ORGANISM: Artificial Sequence
<220> FEATURE:
<223> OTHER INFORMATION: Description of Combined DNA/RNA Molecule:
      DNA/RNA triplex

<400> SEQUENCE: 17
cucucucucu cucucucucu cucuagagag agagagagag agagagagcu cucucucucu        60
cucucucucu cu                                                            72
```

CONVERSION OF A WATSON-CRICK DNA TO A HOOGSTEEN-PAIRED DUPLEX

This Application is a Continuation-in-Part of Ser. No. 09//357,424 filed Jul. 20,1999.

FIELD OF THE INVENTION

The present invention generally relates to the field of therapeutic and diagnostic nucleic acid preparatives, as a novel Hoogsteen duplex structure that can be used to selectively hybridize with a target third RNA or DNA strand by Watson-Crick pairing, thus forming a triplex, is disclosed. The present invention also relates to the field of "antisense" therapy, as a method whereby nucleic acid structures are used to hybridize with mRNA and control gene expression through inhibiting translation, is provided. The invention further relates to the use of "antigene" nucleic acid structures, as these structures are used by the present inventors to hybridize with a strand of DNA and control gene expression by inhibiting transcription.

BACKGROUND OF THE INVENTION

Antisense and antigene control of gene expression are two ol the more promising new biotechnology techniques (1–6). In general, the antisense technology involves the binding of one strand of nucleic acid, which may be normal or modified DNA or RNA, to a target single-stranded sequence in mRNA to form a duplex. The antigene technology generally involves the binding of one strand of nucleic acid, which may be normal or modified DNA or RNA, to a target sequence in the double-stranded DNA genome to form a triplex.

The two major nucleic acid triple-helix motifs with Hoogsteen or reverse-Hoogsteen pairing of a third strand to a DNA duplex, and the numerous ways in which a third strand might inhibit transcription or mediate mutagenesis and recombination in antigene drug therapies, have been reviewed (4–6). There is some evidence that suggests triplexes may form under in vivo conditions (7–14), and may involve RNA (15). With RNA as one or more of the strands, triple helix formation could potentially be used to control biological processes that encompass mRNA, RNA:DNA hybrids, or RNA hairpins.

There are eight possible combinations of DNA and RNA strands in a triplex. Roberts and Crothers (18) explored the effects of backbone composition on pyr*pur:pyr triplex stability using four Watson-Crick-paired hairpin duplexes (D:D, D:R, R:D, and R:R) having 12 base pairs, including 8 G:C pairs, in the stems. These were mixed with homopyrdimidine DNA (D) or RNA (R) 12-mers of the proper sequences to form Hoogsteen pairs. At pH 5.5, the D*R:D and D*R:R triplexes did not form. In general, a triplex was formed with a Hoogsteen DNA pyrimidine strand only when it could pair with a DNA purine strand. Melting was by Scheme I or II of FIG. 1. Four triplexes (D*D:D, D*D:R, R*R:D, and R*R:R) melted with two transitions, with the lower $T_m$ values corresponding to the separation of the third Hoogsteen-paired strand. Only one, or two very close, transitions were found for the R*D:D and R*D:R triplexes, indicating that the Hoogsteen-paired strand was stable until the hairpin duplex melted. Noronha and Damha (19, 20) confirmed and extended the Roberts and Crothers (18) results with the same hairpin duplex sequences. Other workers used relatively long Watson-Crick duplexes to make partial triplexes with short Hoogsteen-paired third strands (21–23). Again it was found that the D*R:D and D*R:R triplexes did not form, R*D:D and R*D:R were among the most stable triplexes, and the shorter Hoogsteen-paired oligomers always melted at a lower temperature than the Watson-Crick duplexes.

Many studies of triplexes, including NMR and thermodynamic studies, have made use of constructs in which two or all three strands are covalently linked (24–36). The relative stability of the Hoogsteen-paired strand is more certain when mixtures are made of separated oligomers. Liu et al. (37) recognized that unlinked strands can form a Hoogsteen-paired DNA duplex at pH 5.1. The strand sequences were constructed so that an antiparallel Watson-Crick alignment would not be stable. Whether Watson-Crick or Hoogsteen duplexes are more stable in mixtures of separate strands depends on the sequences and conditions involved (17, 18, 38). Lavelle and Fresco (17) inferred from optical and thermodynamic studies that the two melting transitions of a d($C^+T$)$_6$*d(AG)$_6$:d(CT)$_6$ (SEQ ID NO: 15) triplex formed from separate strands at pH 4.2 represented (a) a dissociation at lower temperatures of the Watson-Crick pair and (b) the dissociation of a more stable Hoogsteen-paired duplex at higher temperatures. That is, dissociation occurred by Scheme III of FIG. 1. At higher pH values, the Hoogsteen-paired strand was less stable and dissociated first.

SUMMARY OF THE INVENTION

In some aspects, the present invention provides a method of users a preformed double-stranded nucleic acid structure consisting of two parallel Hoogsteen-base-paired strands to bind to a single-stranded target in mRNA or one strand of the double-stranded DNA genome. In both cases, the resulting structure is a triplex.

In the pyrimidine*purine:pyrimidine (pyr*pur:pyr) motif, the subject of this application, the strands are restricted to being all homopurine or homopyrimidine. "*" and ":" respectively denote pairing between parallel Hoogsteen-paired and antiparallel Watson-Crick-paired strands. The pyr*pur:pyr triplex contains protonated $C^+$*G:C base triples, diagrammed at the top of FIG. 1. The G forms 3 hydrogen bonds with one C by Watson-Crick pairing and 2 hydrogen bonds with a second $C^+$ by Hoogsteen pairing. The cytosines of a Hoogsteen pair are protonated at their N3 positions, and the triplex preferentially forms at low pH. However, the pKa for protonation of a hydrogen-bonded cytosine N3 can be well above the pKa of 4.6 for isolated cytidylic acid. The requirement for protonation of Hoogsteen-paired $C^+$ bases leads to enhanced triplex stability at low pH (16,17). It is also possible to form unprotonated T*A:T or U*A:U base triples that are isostructural with the $C^+$*G:C base triple. Thus, these triple helices have all-pyrimidine and all-purine strands arranged as pyr*pur:pyr.

Figure 1:
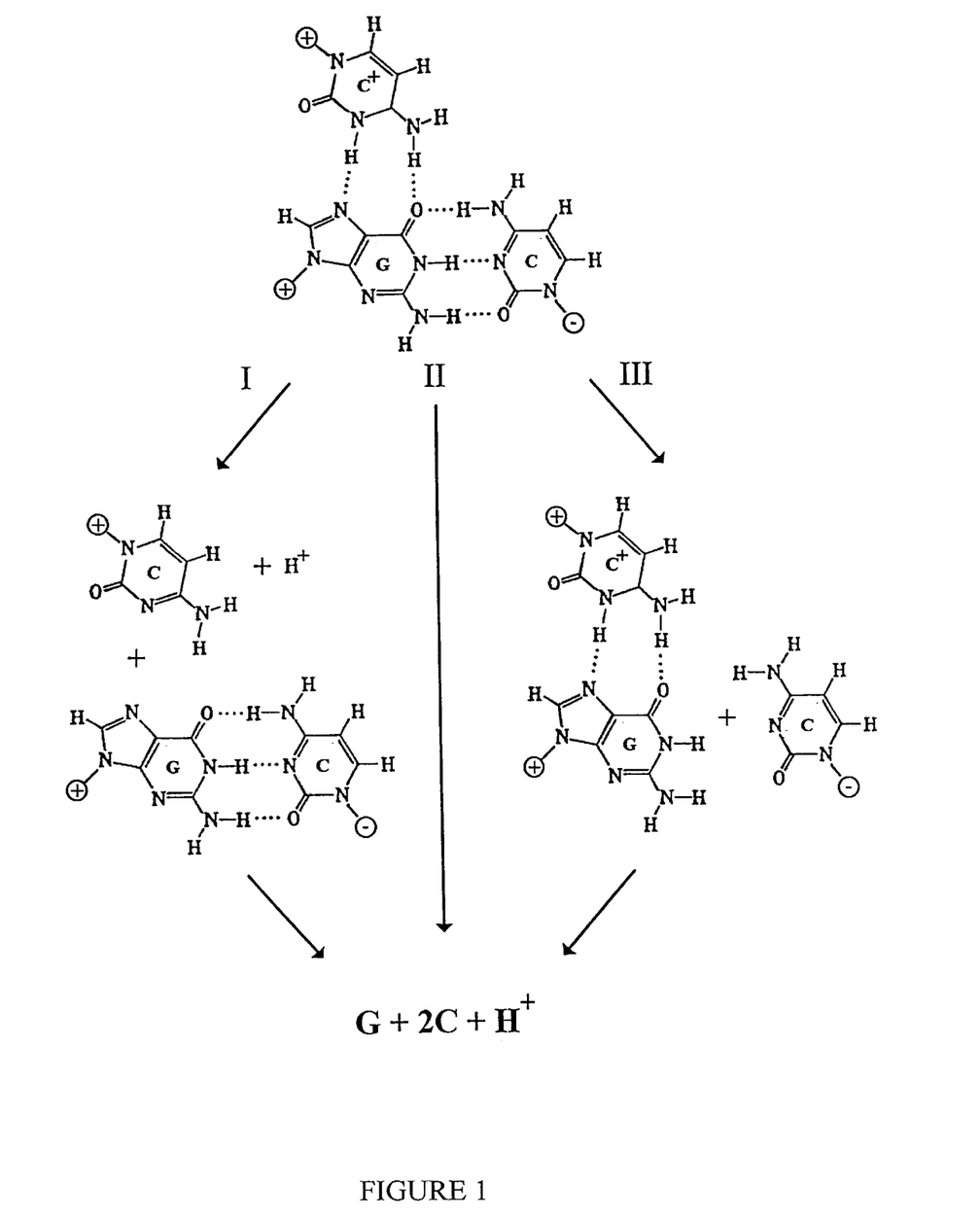
FIG. 1. Three paths for the dissociation of a pyr*pur-pyr triple helix. The $C^{30}$ *G·C base triple at the top of the figure is isostructural with T/U*A·T/U base triples. The strands can be of different allowed combinations of DNA and RNA. The strands containing Hoogsteen $^+$*G pairs are parallel and the strands containing Watson-Crick G·C pairs are antiparallel. Scheme I: strands with Hoogsteen pairs are less stable and dissociate at lower temperatures then the strands with Watson-Crick pairs. Scheme II: the three strands simultaneously dissociate. Scheme III: the strands with Hoogsteen pairs are more stable and dissociate at higher temperatures than the strands with Watson-Crick pairs.

The present inventors have discovered that R*D:R as well as D*D:D triplexes formed from separate d(AG)$_{12}$ and d(CT)$_{12}$ or r(CU)$_{12}$ strands at low pH melt with two transitions by Scheme III of FIG. 1. Thus, the Watson-Crick strand can be preferentially dissociated by increasing the temperature at low pH, resulting in a stable structure consisting of only the Hoogsteen-paired duplex even when the strands are not covalently linked. The Hoogsteen duplex can be an RNA*DNA hybrid or a DNA*DNA duplex. The preferred Hoogsteen duplex is the RNA*DNA hybrid. Covalent linkage of the two strands would provide even greater stability.

The solution constraints and conditions for forming and isolating Hoogsteen-paired duplexes is described in the context of the present invention. A Hoogsteen-paired RNA*DNA hybrid duplex that can bind to a third RNA strand with high affinity is used in one aspect of the present invention as part of a new type of enhanced therapeutic antisense molecule. A Hoogsteen-paired RNA*DNA duplex can bind to a third DNA strand with high affinity, predicted to be higher than that of binding of a DNA*DNA duplex to a third DNA strand, and thus may be used as a new type of enhanced therapeutic antigene molecule.

Antisense DNA drug therapy (39) has been shown in at least some instances to be an effective means of controlling disease processes at the translational level of gene expression. At least 12 clinical trials using antisense methods are underway (1), and progress has been made in treating HIV infection, β-globin thalassemia, stenosis (constriction) of artery-replaced vein grafts, diabetic retinopathy, various cancers, hematological malignancies, malaria, hepatitis B infection, papillomavirus genital warts, and retinitis caused by cytomegalovirus (1, 2). The antisense effect is typically obtained by hybridization of a DNA oligonucleotide (typically about 20 nucleotides long) to a complementary sequence within an mRNA. The hybrid then physically blocks translation or activates RNase H degradation of the mRNA.

Most of the first generation of antisense drugs consist of phosphorothioate DNAs (S-DNAs), in which sulfur replaces one of the phosphodioxy oxygens in each nucleotide subunit of the oligonucleotide. One disadvantage of S-DNAs is that the phosphorothioate substitution reduces the stability of S-DNA:RNA hybrids relative to hybrids with unmodified DNAs (40). A second generation of antisense drugs has base, sugar, and phosphate modifications that enhance hybrid stability. Another strategy to increase the antisense effect is to combine different modifications in a "gapmer" DNA that has other nucleotide modifications flanking an S-DNA segment, which is retained since S-DNA:RNA hybrids activate RNase H (2, 41). General problems that must be solved on a case-by-case basis are that some antisense DNA sequences form competing self-complexes such as hairpins or may bind non-specifically to cellular proteins.

Figure 2:
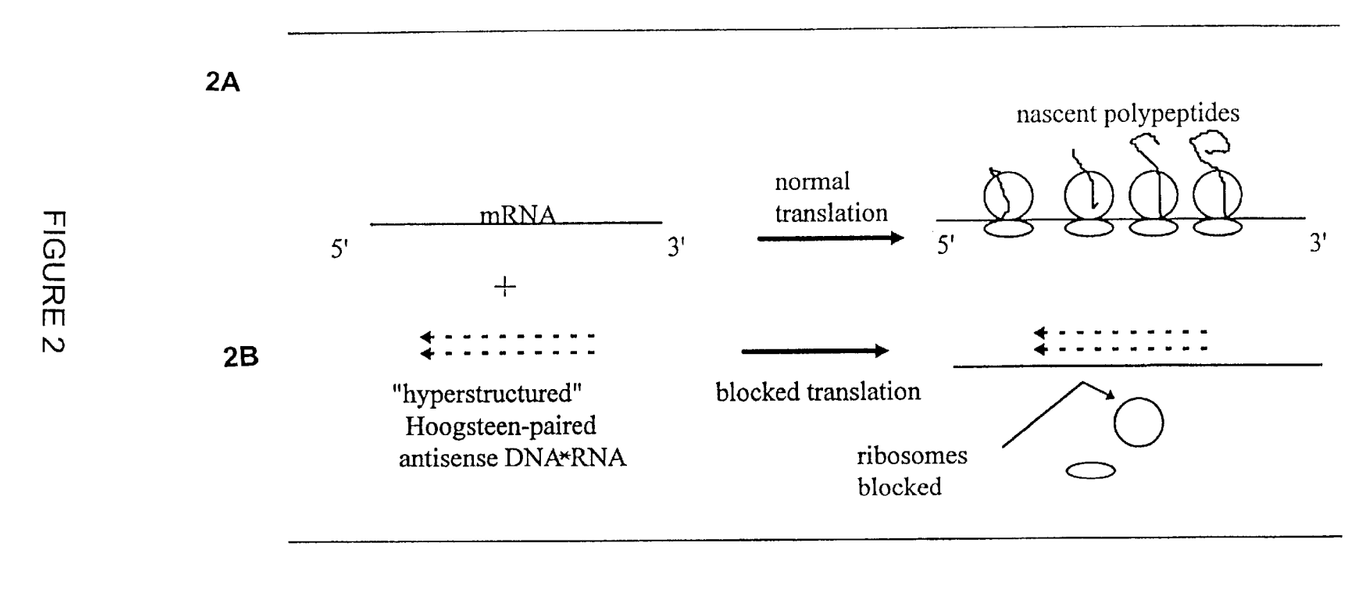

In one aspect the present invention provides a multistranded, or "hyperstructured", antisense molecule. This molecule consists of two parallel-stranded Hoogsteen-paired strands that, compared with single-stranded S-DNAs, are less likely to form self-complexes and would be able to form a more stable complex with a target mRNA by triplex pairing. Triplex formation could either physically block translation, as illustrated in FIG. 2, or be attached to an S-DNA segment to activate RNase H.

The ability of a single stranded DNA or RNA to form a triplex structure is the basis of an "antigene" drug. The result is to control transcription, where the DNA duplex gene is the target (4–6, 39). This use of triplexes differs from that described in the present invention to control transcription. In some embodiments of the invention, the target is one of the single-strands of the duplex, and the antigene molecule is itself a duplex that has Hoogsteen base pairs.

Foldback triplex-forming oligonucleotides (FTFOs) (Kandimalla et al., U.S. Pat. No. 5,693,773 (1997)) consist of a continuous strand with all the nucleotides linked in one 5' to 3' direction. FTFOs fold so that there is an antiparallel arrangement of typically two pyrimidine domains of this molecule that both directly pair with the target. One domain pairs parallel and one domain pairs antiparallel to the target sequence direction. Folding is simultaneous upon forming a triplex.

The stem-loop oligonucleotides (Kool, U.S. Pat. No. 5,808,036 (1998)) consist of a loop region with nucleotides linked in one 5' to 3' direction. Different domains of the loop are like domains of FTFOs in that they typically are pyrimidine rich and both directly pair with the target. Again, one domain pairs parallel and one domain pairs antiparallel to the target sequence direction, and the domains of the loop are not in a duplex form before adding the target nucleic acid.

In other embodiments, the invention comprises a nucleic acid composition comprising two strands or two domains that are parallel and paired prior to forming a triplex. In particular embodiments, the invention provides one pyrimidine strand or domain and one purine strand or domain, with any linkage being such that the strands are linked head-to-head or tail-to-tail and all the nucleotides are not in the same 5' to 3' direction.

BRIEF DESCRIPTION OF THE DRAWINGS

FIGS. 2A and 2B Action of the Hoogsteen-paired antisense RNA*DNA hybrid. FIG. 2A: in normal translation, the mRNA is read by ribosomes and polypeptide chains are produced. FIG. 2B: the addition of a Hoogsteen-paired hybrid to form a Watson-Crick duplex with the mRNA target site could block translation.

FIGS. 3A and 3B. (3A) Example melting profiles of $d(CT)_{12}$ plus $d(AG)_{12}$ mixtures at different pH values.

50% $d(CT)_{12}$ at pH 8 (—); 50% $d(CT)_{12}$ pH 7(— — —); 67% $d(CT)_{12}$ at pH 6.5 (- - -), 67% $d(CT)_{12}$ at pH 6 (o), pH 5.6 (Δ), and pH 5 (▲).

(3B) Example melting profiles of $r(CU)_{12}$ plus $d(AG)_{12}$ mixtures at different pH values. 1:1 (pyr:pur) duplex mixtures at pH 8 (—) and pH 7 (- - -); 2:1 (pyr:pur) mixtures at pH 6.5 (— - - -), 2:1 (pyr:pur) mixtures at pH 6 (open circle), pH 5.6 (open triangle), and pH 5 (closed triangle). Absorption values were at 260 nm, with each profile scaled to 1.0 at 20° C. All samples were in 0.05 M Na$^+$ (phosphate) with total strand concentrations of ≈2.5 μM. More details are in reference 43.

50% $r(CU)_{12}$ at pH 8 (—); 50% $r(CU)_{12}$ pH 7(- - -); 67% $r(CU)_{12}$ at pH 6.5 (— - - ), 67% $d(CT)_{12}$ at pH 6 (o), pH 5.6 (Δ), and pH 5 (▲).

DETAILED DESCRIPTION OF THE PREFERRED EMBODIMENT

The use of a triplex-forming set of three nucleic acid strands as an antisense system in the present invention is as follows:

Strand(1)*Strand(2)+Target=Triplex.

In the pyr*pur:pyr motif (4–6), Strand(1) contains pyrimidines, and Strand(2) contains purines. The target strand contains pyrimidines. Pairing between strand(1) and strand(2) is of the Hoogsteen type and is denoted by the symbol '*'. Classical Watson:Crick pairing is denoted by the symbol ':' The two strands of the Strand(1)*Strand(2) complex form the duplex antisense oligomer (DAO):

Duplex Antisense Oligomer (DAO)=Strand(1)*Strand(2).

The DAO binds to the Target strand by Watson:Crick pairing with Strand(2) of the Strand(1)*Strand(2) complex to form the antisense DAO:Target triplex:

Strand( 1 )*Strand(2):Target=DAO: Target triplex.

There are eight combinations of DNA and RNA strands that can be used to form triplexes. These combinations have been studied by Roberts & Crothers (18), where the Watson-Crick (W:C) paired strands were covalently linked. Six of the eight possible triplex combinations could be formed, as summarized in Table 1. From the Roberts and Crothers (18) data, the RNA*DNA:RNA, RNA*DNA:DNA, RNA*RNA:DNA and RNA*RNA:RNA triplexes have the highest total free energy. See the next-to-last row (C) of Table 1. The RNA*RNA:DNA and RNA*RNA:RNA triplexes, however, melt in two stages, with the Hoogsteen-paired strand melting first. The RNA*DNA:RNA and RNA*DNA:DNA triplexes are unusual in being of especially high stability while having a high Hoogsteen-paired RNA*DNA duplex free energy (row B) that in turn stabilizes the bound Watson:Crick-paired RNA (Target) strand. This will be shown in EXAMPLE 2 below.

One requirement for having a useful DAO is that the stability of the DAO:Target be greater than that of just a simple duplex Strand(2):Target. As shown in Table 1, columns 2 and 4, the stability of the DAO:target triplexes formed with the RNA*DNA DAO is much greater (−9.7 and −13 kcal/mol) than the Watson-Crick stability of one strand binding the DNA or RNA target (which is −2.2 and −1 kcal/mol, respectively).

The use of a DAO as an antisense molecule is meaningful when the target is RNA, and meaningful as an antigene molecule when the target is DNA. In some embodiments, the DAO is the RNA*DNA hybrid. Kandimalla et al. (24) have described a hairpin DNA*DNA molecule that is active in binding DNA or RNA. These hairpin DNA*DNA molecules may be used together with the concepts of the present invention to provide triplexes having stabilities shown in columns 1 and 3 of Table 1. In considering this DNA*DNA DAO molecule, however, it is less effective than the use of the RNA*DNA Hoogsteen-paired DAO of the present invention. This is in part because the final total stability of the triplex that is formed is much lower under the same conditions (pH 5.5, 100 mM sodium acetate, 1 mM EDTA for data in Table 1). That is, the RNA*DNA DAO has an incomparable increase in hybridization efficiency. Calculations of hybridization efficiency to compare these two types of DAO are shown in the last row of numbers in Table g. Th e values of 69% and 99.2% with the RNA*DNA DAO are five orders of magnitude greater than with the DNA*DNA DAO.

Of the remaining triplexes, those in columns 5 and 7 of Table 1, do not form. The triplexes in columns 6 and 8 have low stabilities of the Hoogsteen-paired strand, as described above, and so are not the preferred type of DAO.

Other triplexes include the "fold-back triplex-forming oligonucleotides", (Kandimalla et al. (25, 26, U.S. Pat. No. 5,693,773)), and the circular molecules or stem-loop molecules (Kool and coworkers (28–30, U.S. Pat. No. 5,808,036)), where a purine strand is the target of linked pyrimidine strands which are not at all paired prior to their addition to the third purine strand.

Advantages of the present invention, among others, include a range of targeted sequences that is increased, and an enhanced resistance to nucleases, as the structured nature of the DAO duplex itself could increase its resistance to nucleases without resorting to major chemical modifications, common in other antisense drugs.

TABLE 1

Summary of triplex strand combinations studied by Roberts & Crothers (18) at pH 5.5, 100 mM sodium acetate, 1 mM EDTA, and thermodynamic data from that work.

|  | col. 1 | Present Anti-gene DAO | col. 3 | Present Anti-sense DAO | col. 5 | col. 6 | col. 7 | col. 8 |
| --- | --- | --- | --- | --- | --- | --- | --- | --- |
| Triplex is possible? | Yes | Yes | Yes | Yes | No | Yes | No | Yes |
| Hoogsteen pyrimidine*purine DAO | DNA* DNA | RNA* DNA | DNA* DNA | RNA* DNA | DNA* RNA | RNA* RNA | DNA* RNA | RNA* RNA |
| Watson-Crick pyrimidine - Target | DNA | DNA | RNA | RNA | DNA | DNA | RNA | RNA |
| (A) W-C duplex free energy (kcal/mol)$^1$ | −2.2 | −2.2 | −1 | −1 | −8.5 | −8.5 | −12 | −12 |
| (B) Hoogsteen free energy (kcal/mol) | −0.5 | −7.5 | −1.2 | −12 | NA | −0.5 | NA | −3 |
| (C) Total relative free energy (kcal/mol) | −2.7 | −9.7 | −2.2 | −13 | NA | −9.0$^3$ | NA | −15 |
| % Hybridization$^2$ | 0.0008 | 69.0 | 0.0004 | 99.3 |  |  |  |  |

$^1$All free energies are relative, with the maximum for disruption of the most stable Hoogsteen duplex and disruption of the most stable Watson-Crick duplex being set at 12 kcal/mol.
$^2$The % hybridization is calculated as follows, on the basis of the total free energy of both Watson-Crick and Hoogsteen duplexes. The relative % hybridization is taken to be under conditions where the [DAO] is in excess over the target nucleic acid concentration, and to be present at 100 nM ($10^{-7}$ M) concentration (following ref. 42), at 37° C.:Hybridization ratio = [DAO:target]/[target] = [DAO] exp(−ΔG°/RT), using the definition of equilibrium constant K = exp(−ΔG°/RT) = [DAO:target]/([DAO][target]) For−13 kcal/mol, the hybrridzation ratio = [DAO] exp(−ΔG°/RT) = $10^{-7}$ exp(+13/(1.987 × $10^{-3}$ × 310) = 146. Therefore, the % hybridization = 100*146/(146 + 1) = 99.3%.
$^3$There is an error of about 3 kcal/mol in the total given in Roberts and Crothers (18).

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Figure 3:
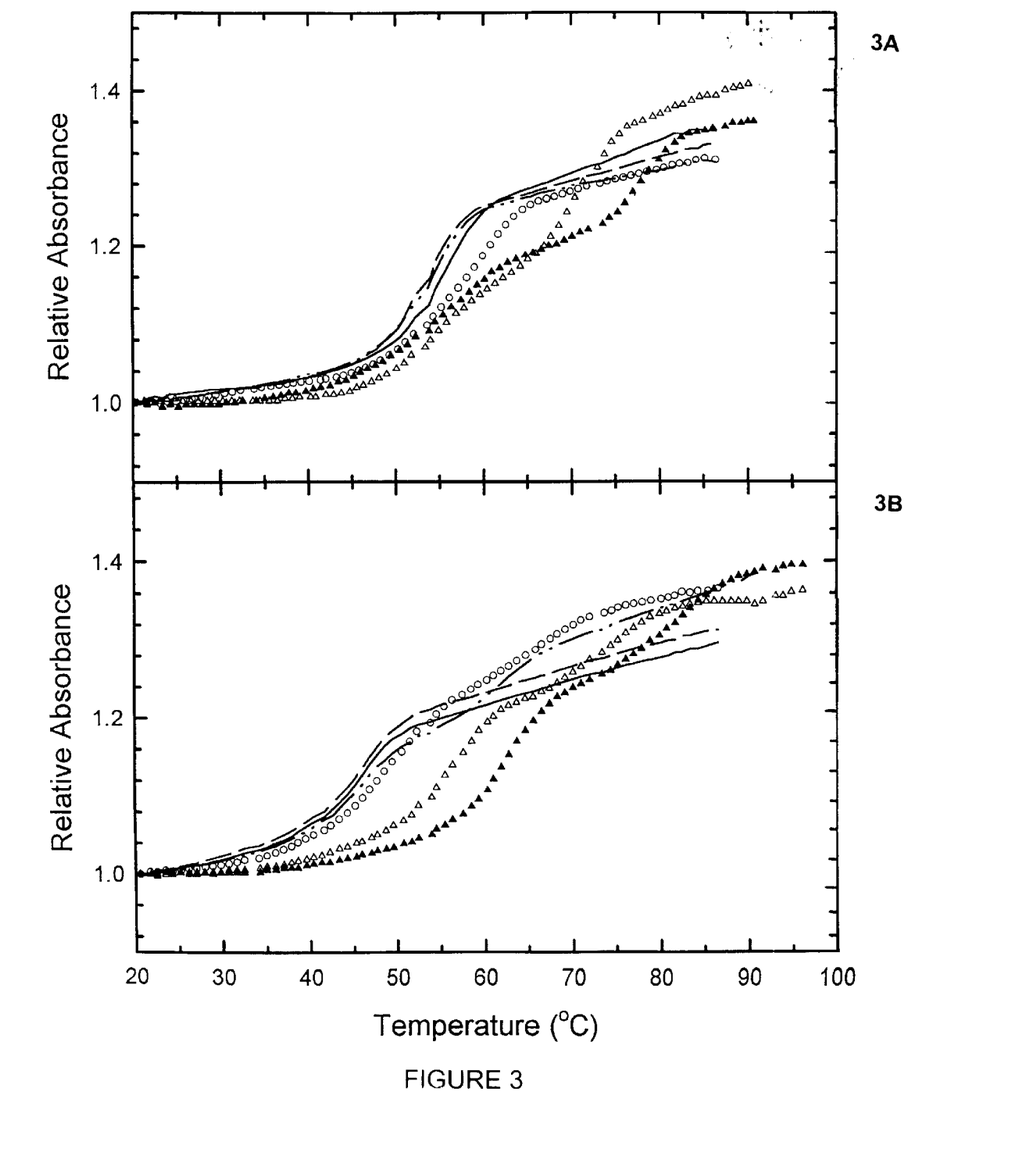

FIG. 3(A) shows representative melting profiles for mixtures of d(CT)$_{12}$ plus d(AG)$_{12}$ at the various pH values.

Melting temperatures are summarized in Table 2. This example shows that it is possible to isolate a Hoogsteen-paired DNA*DNA duplex by heating a DNA*DNA:DNA triplex to 65° C. to release the d(CT)$_{12}$ (target) strand. The triplex is:

5'-d(-CTCTCTCTCTCTCTCTCTCTCTCT)-3' (strand 1) (SEQ ID NO:1)

5'-d(AGAGAGAGAGAGAGAGAGAGAGAG-)-3' (strand 2) (SEQ ID NO:2)

3'-d(TCTCTCTCTCTCTCTCTCTCTCTC-)-5' (target) (SEQ ID NO:3)

TABLE 2

Melting temperatures for 1:1 and 2:1 mixtures of d(CT)$_{12}$ plus d(AG)$_{12}$ in 0.05 mM Na$^+$ (phosphate) at various pH values.

| Strands mixed | pH | Structure | 1st T$_m$ (° C.) | 2nd Tm (° C.) | % full length d(AG)$_{12}$[a] |
|---|---|---|---|---|---|
| d(CT)$_{12}$ plus d(AG)$_{12}$ | 8 | Duplex | 55.2 ± 0.3[b] | none | |
| | 7 | Duplex | 54.5 ± 0.6 | none | |
| | 6.5 | 2:1 Mixture | 54.1 ± 0.4 | none | |
| | 6 | 2:1 Mixture | 58.6 ± 1.3 | none | |
| | 5.6 | Triplex | 55.4 ± 0.5 | 71.8 ± 0.8 | 95 ± 1 |
| | 5 | Triplex | 56.9 ± 0.9 | 77.6 ± 0.6 | 84 ± 3 |

[a]Determined as the end-labeled material remaining in a single band, relative to untreated d(AG)$_{12}$, after heating to 90° C. at the same pH and at the same rate as used for the melting profile. Errors are ranges from duplicate measurements.
[b]T$_m$ values and errors are the averages and standard deviations from at least six independent melting profiles.

The duplexes of d(CT)$_{12}$ plus d(AG)$_{12}$ at the highest pH values melted with one transition at 54.5–55.2° C. that represented dissociation of the Watson-Crick duplex (FIG. 3A and Table 2). The 2:1 mixture at pH 6.5 also dissociated with a T$_m$ characteristic of the Watson-Crick duplex. At pH 6, there was evidence for the influence of a triplex component in the 2:1 (pyr:pur) mixture because the T$_m$ of this sample was higher (58.6° C.) than that of the duplex. At pH 5.6 and 5 the triplexes of d(CT)$_{12}$ plus d(AG)$_{12}$ melted with two clear transitions, both of which were cooperative. The first transition was close to that of the duplex, while the second transition was at a much higher temperature which increased from 72 to 78° C. as the pH decreased from 5.6 to 5. This second transition was that of the Hoogsteen-paired duplex. The initial mixtures of strands have been shown to be Watson-Crick duplexes at the highest pH values and pyr*pur:pyr triplexes at the lowest pH values (43).

Consistent with the data in Table 1, the pairing of the Hoogsteen DAO to the purine strand did not greatly increase the 1st T$_m$ of the Watson-Crick paired duplex.

EXAMPLE II

FIG. 3(B) shows representative melting profiles for mixtures of d(CT)$_{12}$ plus d(AG)$_{12}$ at the various pH values. Melting temperatures are summarized in Table 3. This example shows that it is possible to isolate a Hoogsteen-paired RNA*DNA duplex by heating an RNA*DNA:RNA triplex to 70° C. to release the r(CU)$_{12}$ (target) strand. The triplex is:

5'-r(CUCUCUCUCUCUCUCUCUCUCUCU)-3' (strand 1) (SEQ ID NO: 4)

5'-d(AGAGAGAGAGAGAGAGAGAGAGAG)-3' (strand 2) (SEQ ID NO: 5)

3'-r(UCUCUCUCUCUCUCUCUCUCUCUC)-5' (target) (SEQ ID NO: 6)

TABLE 3

Melting temperatures for 1:1 and 2:1 mixtures of r(CU)$_{12}$ plus d(AG)$_{12}$ in 0.05 mM Na$^+$ (phosphate) at various pH values.

| Strands mixed | pH | Structure | 1st T$_m$ (° C.) | 2nd Tm (° C.) | % full length d(AG)$_{12}$[a] |
|---|---|---|---|---|---|
| r(CU)$_{12}$ plus d(AG)$_{12}$ | 8 | Duplex | 45.7 ± 0.4 | none | |
| | 7 | Duplex | 45.5 ± 0.5 | none | |
| | 6.5 | 2:1 Mixture | 46.9 ± 0.8 | 62.4 ± 0.6 | |
| | 6 | Triplex | 52.5 ± 1.3 | 66.1 ± 0.4 | |
| | 5.6 | Triplex | 57.2 ± 1.7 | 75.2 ± 1.8 | 95 ± 1 |
| | 5 | Triplex | 62.8 ± 0.7 | 80.8 ± 0.7 | 84 ± 3 |

[a]Determined as the end-labeled material remaining in a single band, relative to untreated d(AG)$_{12}$, after heating to 90° C. at the same pH and at the same rate as used for the melting profile. Errors are ranges from duplicate measurements.
[b]T$_m$ values and errors are the averages and standard deviations from at least six independent melting profiles.

A dramatic effect of pH was evident on the melting temperatures of mixtures of the RNA, r(CU)$_{12}$, and the DNA, d(AG)$_{12}$. At pH 8 and 7, the Watson-Crick duplexes melted with one transition at 45.5–45.7 C. (FIG. 3B and Table 3). The melting profiles of the 2:1 (pyr:pur) mixtures at acidic pH values exhibited two cooperative transitions, and the T$_m$ values of both transitions increased as the pH decreased. In this case, the stabilities of the Watson-Crick and Hoogsteen-paired duplexes were both increased by cytosine protonation. This second transition was that of the Hoogsteen-paired duplex. The initial mixtures of strands have been shown to be Watson-Crick duplexes at high pH values and pyr*pur:pyr triplexes at low pH values (43).

Consistent with the data in Table 1, the pairing of the Hoogsteen DAO to the purine strand substantially increased the 1st T$_m$ of the Watson-Crick paired duplex.

In summary, EXAMPLES 1 and 2 show that the triplexes of d($^+$T)$_{12}$*d(AG)$_{12}$:d(CT)$_{12}$ (SEQ ID NO:16 and (SEQ ID NO:17) r(C$^+$U)$_{12}$*d(AG)$_2$:r(CU)$_{12}$ at pH 5.6 and 5 melted with two cooperative transitions, the second of which was at an unusually high temperature and was pH-dependent. Depurination during heating was minimal (last columns of Tables 2 and 3), there were no unexpected structures in the mixtures, and strands separated in the first melting transition did not reform stable structures. Finally, the transitions were characteristically different for the DNA and hybrid triplexes. The higher T$_m$ values for the triplexes were from melting of the Hoogsteen duplexes and the triplexes melted by Scheme III of FIG. 1. The pH-dependence of the second transition is in accord with the involvement of a protonated cytosine in a Hoogsteen $^+$*G base pair. The influence of pH on the first transition (of the Watson-Crick duplex) indicated that the third Hoogsteen-paired strand also stabilized the Watson-Crick base pair, especially in the case of the hybrid triplex. Although at pH 7 or 8 the hybrid duplex had a lower T$_m$ than did the DNA duplex, at low pH both transitions of the hybrid triplex were actually increased to be at higher temperatures than those of the DNA triplex. That is, at low pH both types of base pairing were relatively more stable in the conformation of the hybrid triplex (compared with those of the DNA triplex).

EXAMPLE III

The following is an illustration to make clear the form and potential of the invention. DNA and RNA strands can be linked at their 5'—5' ends by normal chemical synthesis of the RNA strand in the 3' to 5' direction followed by the addition of DNA nucleotides in the 5' to 3' direction using reverse chemical synthesis. This can be done commercially, e.g. by Oligos Etc., Inc., Wilsonville, Oreg.

(SEQ ID NO:12) 3'-r(UUUCUCCCUUC)-5'-5'-d(TTTTGAAGG-GAGAAA)-3'. (SEQ ID NO: 7)

A short linker of four T residues allows the strands to form a hairpin Hoogsteen-paired duplex:

This duplex can then make Watson-Crick pairs with a target sequence in a mRNA such as 5'-r(UUUCUCCCUUC)-3' (SEQ ID NO: 9)

to form a triplex:

The target sequence does occur within the mRNA of brome mosaic virus. This example illustrates that linked Hoogsteen-paired parallel strands can be made, and that the requirement for having a polypyrimidine target sequence is met within natural sequences.

The following references, to the extent that they provide exemplary procedural or other details supplementary to those set forth herein, are specifically incorporated herein by reference.

REFERENCES

1. Matteucci, M. D, & Wagner, R. W. (1996) *Nat.* 384, 20–22.
2. Rouhi, M. (1997) Chemical & Eng. News 74, 38–39, report on "Antisense '97" Conference, Cambridge, Mass., May 1–2, 1997 (plus information in conference Book of Abstracts).
3. Orr, R. M. & Monia, B. P. (1998) Cur. Res. Molecular Therapeutics 1, 102–108.
4. Thoung, N. T. and Helene, C. (1993) *Angew. Chem.*, 32, 666–690.
5. Radharkrishnan, I. and Patel, D. J. (1994) *Biochemistry*, 33, 11405–11416.
6. Chan, P. P. and Glazer, P. M. (1997) *J. Mol. Med.*, 75, 267–282.
7. Collier, D. A. and Wells, R. D. (1990) *J. Biol. Chem.*, 265, 10652–10658.
8. Potaman, V. N. and Sinden, R. R. (1998) *Biochemistry*, 37, 12952–12961.
9. Kiyama, R. and Camerini-Otero, R. D. (1991) Proc. Natl. Acad. Sci. USA, 88, 10450–10454.
10. Svinarchuk, F., Debin, A., Bertrand, J.-R. and Malvy, C. (1 996) Nucleic Acids Res., 24, 295–302.
11. Debin, A., Malvy, C. and Svinarchuk, F. (1997) *Nucleic Acids Res.*, 25, 1965–1974.
12. Kim, H.-G. and Miller, D. M. (1998) *Biochemistry*, 37, 2666–2672.
13. Grigoriev, M., Parseuth, D., Guieysse, A. L., Robin, P., Thuong, N. T., Hélène, C. and Harel-Bellan, A. (1993) Proc. Natl. Acad. Sci.USA, 90, 3501–3505.
14. Guieysse, A.-L., Praseuth, D., Grigoriev, M., Harel-Bellan, A. and Hélène, C. (1996) *Nucleic. Acids Res.*, 24, 4210–4216.
15. McDonald, C. D. and Maher, L. J., III (1995) *Nucleic Acids Res.*, 23, 500–506.
16. Keppler, M. D. and Fox, K. R. (1997) *Nucleic Acids Res.*, 25, 4644–4649.
17. Lavelle, L. and Fresco, J. R. (1995) *Nucleic Acids Res.*, 23, 2692–2705.
18. Roberts, R. W. and Crothers, D. M. (1992) *Science*, 258, 1463–1466.
19. Noronha, A. and Damha, M. J. (1998) *Nucleic Acids Res.*, 26, 2665–2671.
20. Damha, M. J. and Noronha, A. (1998) *Nucleic Acids Res.*, 26, 5152–5156.
21. Escudé, C., Francois, J. -C., Sun, J. -S., Ott, G., Sprinzl, M., Garestier, T. and Hélène, C. (1993) *Nucleic Acids Res.*, 21, 5547–5553.
22. Han, H. and Dervan, P. B. (1993) *Proc. Nucl. Acad. Sci. USA*, 90, 3806–3810.
23. Han, H. and Dervan, P. B. (1994) *Nucleic Acids Res.*, 22, 2837–2844.
24. Kandimalla, E. R., Agrawal, S., Venkataraman, G. and Sasisekharan, V. (1995) *J. Am. Chem. Soc.*, 117, 6416–6417.
25. Kandimalla, E. R., Manning, A. N. and Agrawal, S. (1995) *J. Biomol. Struct. Dyn.*, 13, 483–491.
26. Kandimalla, E. R., Manning, A. and Agrawal, S. (1996) *J. Biomol. Struct. Dyn.*, 14, 79–90.
27. Mundt, A. A., Crouch, G. J., and Eaton, B. E. (1997) *Biochemistry*, 36, 13004–13009.
28. Wang, S. and Kool, E. T. (1995) *Biochemistry*, 34, 4125–4132.
29. Wang, S. and Kool, E. T. (1995) *Nucleic Acids Res.*, 23, 1157–1164
30. Wang, S., Friedman, A. E. and Kool, E. T. (1995) *Biochemistry*, 34, 9774–9784.
31. Völker, J., Botes, D. P., Lindsey, G. G. and Klump, H. H. (1993) *J. Mol. Biol.*, 230, 1278–1290.
32. Plum, G. E. and Breslauer, K. J. (1995) *J. Mol. Biol.*, 248, 679–695.
33. Bartley, J. P., Brown, T. and Lane, A. N. (1997) *Biochemistry*, 36, 14502–14511.
34. Gacy, A. M., Goellner, G. M., Spiro, C., Chen, X., Gupta, G., Bradbury, E. M., Dyer, R. B., Mikesell, M. J., Yao, J. Z., Johnson, A. J., Richter, A., Melangon, S. B. and McMurray, C. T. (1998) *Molecular Cell*, 1, 583–593.
35. Blommers, M. J. J., Natt, F., Jahnke, W. and Cuenoud, B. (1998) *Biochemistry*, 37, 17714–17725.
36. Gotfredsen, C. H., Schultze, P. and Feigon, J. (1998) *J. Am. Chem. Soc.*, 120, 4281–4289.
37. Liu, K., Miles, H. T., Frazier, J. and Sasisekharan, V. (1993) *Biochemistry*, 32, 11802–11809.
38. Bhaumik, S. R., Kandala, V. R., Govil, G., Liu, K. and Miles, H. T. (1995) *Nucleic. Acids Res.*, 23, 4116–4121.
39. Cohen, J. S. (1989) "Oligonucleotides: Antisense Inhibitors of Gene Expression." CRC Press, Boca Raton, Fla.
40. Hashem, G. M., Pham, L., Vaughan, M. R. and Gray, D. M. (1998) *Biochemistry*, 37, 61–72.
41. Monia, B. P., Lesnik, E. A., Gonzalez, C., Lima, W. F., McGee, D., Guinosso, C. J., Kawasaki, A. M., Cook, P. D., and Freier, S. M. (1993) *J. Biol. Chem.* 268, 14514–14522.
42. Freier, S. M., Lima, W. F., Sanghvi, Y. S., Vickers, T., Zounes, M., Cook, P. D., and Ecker, D. J. (1992) in "Gene Regulation: Biology of Antisense RNA and DNA" (Eds. Erickson, R. P., & Izant, J. G.) Raven Press, New York, N.Y., pp. 95–107.
43. Hashem, G. M., Wen, J. -D., Do, Q. and Gray, D. M. (1999) *Nucleic Acids Res.* 27, 3371–3379.

What is claimed is:

1. A method for providing a nucleic acid molecule comprising a Hoogsteen-paired RNA*DNA pyrimidine*purine duplex capable of being used as an antisense molecule comprising:
   preparing a pyr*pur:pyr RNA*DNA:RNA triplex;
   separating a Watson-Crick paired pyrimidine strand by heating to above the melting transition for the Watson-Crick paired strand; and
   removing a pyr*pur Hoogsteen duplex, wherever said duplex has sufficient stability to bond to a target mRNA sequence by Watson-Crick base pairing.

2. The method of claim 1, when the pyr*pur Hoogsteen duplex is removed by gel electrophoresis.

3. The method of claim 1, wherein the Hoogsteen-paired duplex is made by linking the RNA and DNA strands into a Hoogsteen-paired duplex at their 5' ends or at their 3' ends.

4. The method of claim 1, wherein said nucleic acid molecule is a two-stranded antisense molecule comprising at least one protonated C$^{+}$*G Hoogsteen pair.

5. The method of claim 1, wherein said nucleic acid molecule is a two-stranded antisense molecule comprising at least one T*A Hoogsteen pair.

6. The method of claim 1 wherein the Hoogsteen-paired DNA strand duplex is capable of recognizing an mRNA sequence to form a stable triplex complex.

7. A method for providing a nucleic acid molecule capable of being used as an antigene molecule comprising:
   forming and isolating a Hoogsteen-paired RNA*DNA pyrimidine*purine duplex that is capable of binding to a target DNA sequence by Watson-Crick base pairing, wherein said Hoogsteen-paired RNA*DNA pyrimidine*purine duplex is prepared by:
   preparing a pyr*pur:pyr RNA*DNA:RNA triplex;
   separating a Watson-Crick paired pyrimidine strand by heating to above a defined melting transition for the Watson-Crick paired strand, and
   removing the desired pyr*pur Hoogsteen duplex.

8. The method of claim 7 wherein a desired pyr*pur Hoogsteen duplex is removed by gel electrophoresis.

9. The method of claim 7, wherein the Hoogsteen-paired duplex is prepared by a method of linking the RNA and DNA strands into a Hoogsteen-paired duplex at their 5' ends or at their 3' ends.

10. The method of claim 7, wherein said antigene molecule is a two-stranded antisense molecule comprising at least one protonated C$^{+}$*G Hoogsteen pair.

11. The method of claim 7, wherein said antigene molecule is a two-stranded antisense molecule comprising at least one T*A Hoogsteen pair.

12. A triplex nucleic acid structure comprising:
   a first strand, 5'-r(CUCUCUCUCUCUCUCUCUCUCUCU)-3' (strand 1) SEQ ID NO: 4); and
   a second strand, 5'-(AGAGAGAGAGAGAGAGAGAGAGAG)-3' (SEQ ID NO: 5);
   a third stand, 3'-r(UCUCUCUCUCUCUCUCUCUCUCUC)-5' (target) (SEQ ID NO: 6).

13. A triplex nucleic acid structure comprising a linked RNA*DNA duplex capable of recognizing an RNA sequence to form a stable triplex complex of:

```
a duplex structure,   (SEQ ID NO: 14)  3'-r(UUUCUCCCUUC)-T-T
                                                           | (SEQ ID NO: 10); and
                                       3'-d(AAAGAGGGAAG)-T-T a third strand,                        5'-r(UUUCUCCCUUC)-3'.  (SEQ ID NO: 11).
```

14. A triplex nucleic acid structure comprising:
a first RNA strand and second DNA strand, wherein said first RNA strand comprises at least one pyrimidine base and said second DNA strand comprises at least one purine base, wherein said first RNA and second DNA strand pairs by Hoogsteen base pairing; and
a third RNA strand comprising a target RNA sequence capable of forming a triplex nucleic acid structure by pairing of the second DNA strand with a target RNA strand by Watson-Crick base pairing.

15. The triplex nucleic acid structure of claim 14 wherein the target is an mRNA having a sequence 5'-r(UUUCUCCCUUC)-3' (SEQ ID NO: 9).

16. The triplex nucleic acid structure of claim 14 wherein the first RNA and second DNA strand form an antisense molecule to make a triplex with a target RNA sequence.

17. The triplex nucleic acid structure of claim 14 wherein the first RNA and second DNA strand form an antisense molecule to make a triplex with a target RNA sequence to control gene expression.

18. A triplex nucleic acid structure comprising:
a first RNA strand and second DNA strand with said first strand containing at least one pyrimidine base and said second strand containing at least one purine base;
wherein send first RNA strand and said second DNA strand pairs by Hoogsteen base pairing; and
a triplex nucleic acid structure is formed by pairing of the second DNA strand with a target DNA strand by Watson-Crick base pairing.

19. The triplex nucleic acid structure of claim 18 wherein the first RNA strand and second DNA strand form an antigene molecule to form a triplex nucleic acid structure when paired with a target DNA sequence.

20. The triplex nucleic acid structure of claim 18 wherein the first RNA and second DNA strand form an antigene molecule to make a triplex with a target DNA sequence to control gene expression.

21. A double-stranded nucleic acid structure comprising two parallel Hoogsteen base-paired strands having binding affinity for a single-stranded target in a mRNA sequence or one strand of a DNA sequence; wherein said double-stranded nucleic acid structure is capable of binding through Watson-Crick pairing to said single-stranded target in the mRNA sequence or one strand of the DNA sequence to provide a nucleic acid triple-helix motif.

22. An antisense therapeutic molecule comprising:
a Hoogsteen-paired RNA*DNA hybrid duplex capable of binding to a third RNA strand with high affinity.

23. The antisense therapeutic molecule of claim 22 further defined as a Duplex Antisense Oligomer (DAO), wherein the target is RNA.

24. The antigene molecule of claim 23 wherein the DAO is a RNA*DNA hybrid.

* * * * *

UNITED STATES PATENT AND TRADEMARK OFFICE
CERTIFICATE OF CORRECTION

PATENT NO.    : 6,362,322 B1
DATED         : March 26, 2002
INVENTOR(S)   : Donald M. Gray et al.

It is certified that error appears in the above-identified patent and that said Letters Patent is hereby corrected as shown below:

Column 1,
Line 23, replace "ol" with -- of --.

Column 2,
Line 23, replace "users" with -- using --.

Column 3, line 67 - Column 4, line 1,
Replace "pyridimine" with -- pyrimidine --.

Column 4,
Line 8, replace "$C^{30}$*G·C" with -- $C^+$*G:C --.
Line 9, replace "T/U*A·T/U" with -- T/U*A:T/U --.
Line 11, replace "$^+$*G" with -- $C^+$*G --.
Line 12, replace "G.C" with -- G:C --.
Line 14, replace "then" with -- than --.
Line 28, replace "6.5 (---)" with -- 6.5 (— --) --.

Column 5,
Line 67, replace "Table g" with -- Table 1 --.
Line 51, (second-to-last Line of footnote in Table 1) replace "310)" with -- 310 --.

Column 7,
Line 8, replace "5'-d(-CTCTCTCTCTCTCTCTCTCTCT) -3' " with
-- 5'-d(CTCTCTCTCTCTCTCTCTCTCT) -3' --.
Line 11, replace "5' -d(AGAGAGAGAGAGAGAGAGAGAG-) -3' " with
-- 5' -d(AGAGAGAGAGAGAGAGAGAGAG) -3' --.
Line 13, replace "3' -d(TCTCTCTCTCTCTCTCTCTCTC-) -5' " with
-- 3' -d(TCTCTCTCTCTCTCTCTCTCTC) -5' --.

Column 8,
Line 43, replace "d($^+$T)$_{12}$" with -- d($C^+$T)$_{12}$ --.
Line 44, replace "(AG)$_2$" with -- (AG)$_{12}$ --.
Line 54, replace "$^+$*G" with -- $C^+$*G --.

UNITED STATES PATENT AND TRADEMARK OFFICE
CERTIFICATE OF CORRECTION

PATENT NO.    : 6,362,322 B1
DATED         : March 26, 2002
INVENTOR(S)   : Donald M. Gray et al.

It is certified that error appears in the above-identified patent and that said Letters Patent is hereby corrected as shown below:

<u>Column 9,</u>
Line 24, replace "3' -r(UUUCUCCUUC) -T-T" with
-- 3' -r(UUUCUCCCUUC) -T-T --.

<u>Column 10,</u>
Line 44, replace "Melangon" with -- Melancon --.

Signed and Sealed this

Twenty-eighth Day of January, 2003

JAMES E. ROGAN
*Director of the United States Patent and Trademark Office*